United States Patent [19]

Schmidt et al.

[11] 4,288,558

[45] Sep. 8, 1981

[54] PROCESS FOR THE MANUFACTURE OF OXYGEN-CONTAINING CARBON COMPOUNDS FROM SYNTHESIS GAS

[75] Inventors: Hans-Joachim Schmidt, Königstein; Friedrich Wunder, Flörsheim am Main; Hans-Jürgen Arpe, Kelkheim; Ernst I. Leupold, Neu-Anspach, all of Fed. Rep. of Germany

[73] Assignee: Hoechst Aktiengesellschaft, Frankfurt, Fed. Rep. of Germany

[21] Appl. No.: 136,270

[22] Filed: Apr. 1, 1980

Related U.S. Application Data

[63] Continuation of Ser. No. 25,033, Mar. 29, 1979, abandoned.

[30] Foreign Application Priority Data

Apr. 4, 1978 [DE] Fed. Rep. of Germany ....... 2814365
Jun. 10, 1978 [DE] Fed. Rep. of Germany ...... 2825495
Nov. 18, 1978 [DE] Fed. Rep. of Germany ....... 2850110

[51] Int. Cl.³ .............................................. C07C 27/06
[52] U.S. Cl. ..................................... 518/716; 252/441
[58] Field of Search ....... 260/449 R, 449 M, 449.6 R, 260/449.6 M

[56] References Cited

U.S. PATENT DOCUMENTS

| | | | |
|---|---|---|---|
| 4,014,913 | 3/1977 | Ellgen et al. | 260/449 R |
| 4,096,164 | 6/1978 | Ellgen et al. | 260/449 R |
| 4,125,553 | 11/1978 | Cropley | 260/449 R |
| 4,136,104 | 1/1979 | Hwang et al. | 260/449 R |

*Primary Examiner*—Howard T. Mars
*Attorney, Agent, or Firm*—Curtis, Morris & Safford

[57] ABSTRACT

Acetic acid, ethanol, acetaldehyde and possibly secondary products thereof are prepared by the catalytic reaction of carbon monoxide and hydrogen. The catalyst contains, applied onto a carrier, salts or complex compounds of rhodium with a valence below 3, halide ions and salts or complex compounds of magnesium.

13 Claims, No Drawings

PROCESS FOR THE MANUFACTURE OF OXYGEN-CONTAINING CARBON COMPOUNDS FROM SYNTHESIS GAS

This is a continuation of application Ser. No. 025,033 filed Mar. 29, 1979, now abandoned.

The invention provides a process for the manufacture of oxygen-containing carbon compounds having preferably 2 carbon atoms in the molecule, especially the manufacture of acetic acid, ethanol, acetic aldehyde and possibly the secondary products thereof, by reaction of carbon monoxide with hydrogen.

The formation of oxygen-containing carbon compounds having at least 2 carbon atoms in the molecule during reactions of synthesis gas, that is, mixtures of carbon monoxide and hydrogen, in the presence of catalysts of various compositions is known from numerous publications and processes. However, these compounds are generally obtained only as by-products or with a less specific, broad product distribution, that is, products wherein the concentration of the individual components is very low so that processes of this type are of no interest for an economic preparation of the desired products.

It is further known from German Auslegeschriften Nos. 2,503,233 and 2,503,204 that contrary to other catalyst systems the reaction in the gaseous phase of synthesis gas in the presence of rhodium metal-containing catalysts yields substantially mixtures of oxygen-containing products having 2 carbon atoms in the molecule, such as acetic acid, ethanol and/or acetaldehyde. The selectivity with respect to the individual compounds depends on the reaction conditions and can be influenced in favor of ethanol by adding iron salts. Furthermore it is disclosed in German Offenlegungsschrift No. 2,628,463 that manganese may act as a cocatalyst thus improving the activity of the rhodium metal catalysts.

The latter processes are based upon the use of rhodium metal as a catalytically active component. Therefore, the conditions chosen for the preparation of the catalysts are such as to insure a practically quantitative formation of metallic rhodium. For example, rhodium chloride or rhodium dicarbonylacetylacetonate may be reduced in a hydrogen current at a temperature above 300° C., preferably at 450° to 500° C. and, when using rhodium nitrate, the compound may be subjected additionally to pyrolysis prior to reducing it.

In the reaction of synthesis gas on rhodium metal catalysts high activities and space/time yields of more than 400 g of oxygen-containing $C_2$ products per liter of catalyst and hour may be achieved under certain test conditions, but the selectivity towards the desired products is still unsatisfactory. For example, German Auslegeschrift No. 2,503,233 discloses in Table 2 that with the use of a catalyst containing 5 weight % of rhodium metal on silicic acid there is obtained a reaction product containing 42.2 weight % of acetic acid, ethanol and acetaldehyde, which corresponds to a selectivity of 40.2% calculated on the converted carbon monoxide, the residual carbon monoxide is substantially converted to methane and carbon dioxide.

It is, consequently, the object of the present invention to improve the selectivity with respect to oxygen-containing $C_2$ products of rhodium-containing catalysts for the reaction of synthesis gas in order to improve the efficiency of a process of this type for these technologically important intermediate products.

It has now been found that the activity and/or selectivity of the rhodium catalysts depends decisively on the reduction conditions applied during the manufacture of the catalyst and that catalysts having an improved selectivity and/or activity are obtained when maintaining low reduction temperatures. It has been ascertained that this can be attributed to the fact that in these catalysts, contrary to the known catalysts in which rhodium is present in metallic form, rhodium is present not as a metal but as a salt or complex compound with a valence below 3, for example as mono- or bivalent rhodium or as a mixture of these low valency stages. In addition to rhodium, halide ions must be present, optionally in admixture with other anions. It has moreover been found that the activity and/or selectivity of the catalysts of the above type are improved substantially by adding salts or compounds of magnesium as cocatalyst.

Subject of the invention is therefore a process for the manufacture of acetic acid, ethanol, acetaldehyde and possibly secondary products thereof by reaction of carbon monoxide with hydrogen in the presence of rhodium, which comprises using a catalyst applied onto a carrier containing salts or complex compounds of rhodium with a valence below 3, halide ions and as a cocatalyst magnesium in the form of salts or complex compounds.

It was not to be expected that rhodium with a low valence would have a particularly advantageous catalytic activity in the conversion of synthesis gas to oxygen-containing $C_2$ products without being substantially reduced to a metal under the reduction and reaction conditions, since it was known that rhodium salts are reduced quantitatively to rhodium metal under relatively mild conditions, for example at a temperature below 100° C., when treating them with hydrogen (cf. Newkirk et al., J. of Catal. 11(1968), 370). However, it has been ascertained that in the presence of magnesium ions as a cocatalyst and halide ions, the reduction with hydrogen of rhodium salts or complex compounds applied onto a carier at a temperature below 300° C., does not yield metallic rhodium. It has further been ascertained that even when reacting the gas mixture consisting of carbon monoxide and hydrogen under the reaction conditions after extended usage of the catalyst, the low but nonmetallic valency state of rhodium remains substantially unchanged. This is shown by the stable activity of the catalyst displayed at the start of the synthesis gas reaction and after an extended reaction time as well as by the ratio of rhodium and halogen.

Oxygen-containing carbon compounds obtained with high selectivity in the process of the invention are acetic acid, ethanol and/or acetaldehyde, additionally products possibly formed therefrom under the reaction conditions in a subsequent reaction, for example esterification or condensation, such as ethyl acetate and the diethylacetal of acetaldehyde. The amount of other oxygen-containing compounds having 3 or more carbon atoms in the molecule is very low, that is, normally below 5 mol %, relative to reacted carbon monoxide. The total selectivity with respect to oxygen-containing $C_2$ compounds, including products converted to ethyl acetate and acetaldehyde-diethylacetal, is generally up to 90%, relative to reacted carbon monoxide. The remaining carbon monoxide is converted to the cited oxygen-containing products having 3 or more carbon atoms in the molecule, and substantially to methane and other gaseous hydrocarbons including, to a smaller extent, carbon dioxide.

For preparing the catalyst according to the invention halogen-containing salts or complex compounds of rhodium may be used as starting substances. Examples of these compounds are chlorides, bromides and/or iodides of rhodium or double salts with alkali metal halides such as dipotassium trichlororhodate. Furthermore, there may be used halogen-containing complex compounds containing, in addition to rhodium and halogen, complexing ligands such as trialkylphosphine, triarylphosphine, ethylene diamine, pyridine, carbon monoxide, olefins or water, for example tristriphenylphosphine rhodium-I chloride, bromide or iodide, tristriphenylphosphine rhodium-III chloride, dichlorobisethylene diamine rhodium-I chloride, trisethylene diamine rhodium-III chloride, bis-tri-o-tolylphosphine rhodium-II chloride, carbonyl-bis-triphenylphosphine rhodium-I bromide or discesiumcarbonylpentachlororhodate-III. Especially suitable are complex compounds that contain both rhodium and magnesium, for example $Mg_3[RhCl_6]_2$ obtained by reacting magnesium chloride with rhodium chloride in acetic acid at 100° C., or $Mg[Rh(CO)_2Cl_2]_2$ obtained from magnesium chloride and $[Rh(CO)_2Cl_2]_2$ in a mixture of methanol, chloroform and hydrogen chloride at 20° C. under nitrogen.

Furthermore, rhodium compounds may be used wherein rhodium is bound in ionogenic or complex form to a carrier. Examples thereof are zeolites and ion exchangers exchanged with rhodium halides, or rhodium bound in complex form to magnesium silicate. In these compounds further metals may be present in addition to magnesium, for example lithium, beryllium, calcium, manganese, iron, cobalt or nickel.

The catalyst may be prepared by applying the catalytically active salts or complex compounds of the mono- or bivalent rhodium onto a carrier, where they display their catalytic action upon impregnation of a magnesium salt without being reduced. Alternatively, salts or complex compounds of trivalent rhodium may be used and the catalytically active rhodium salts wherein rhodium is present with a valence below 3 in a nonmetallic form, may be obtained upon impregnation by an adequate reduction. This selective reduction may alternatively be performed under the conditions of the synthesis gas reaction, that is by reducing with mixtures of hydrogen and carbon monoxide.

According to the invention, cocatalysts or activators used are salts or complex compounds of magnesium which may be simple inorganic or organic salts of magnesium such as the chloride, bromide, nitrate, formate or acetate of magnesium. The oxide, hydroxide or the carbonates of magnesium may also be used if they are converted into said salts by a treatment with mineral acids or carboxylic acids. Suitable complex compounds include the abovementioned magnesium-rhodium complexes. The magnesium compounds may be applied onto a carrier simultaneously with the rhodium compound. Alternatively, the cocatalytically active magnesium may first be applied onto the carrier or be incorporated in a supporting substance, for example, a silicate- or aluminum oxide-containing carrier substance such as silicic acid, aluminium oxide or aluminum silicate.

A further advantageous method consists in linking magnesium by ion exchange to cation exchangers that are suitable as carriers for rhodium and that are stable under the test conditions, for example, the natural or synthetic aluminum silicates known as molecular sieves. Suitable catalysts may be obtained as well when first impregnating the carrier with the rhodium compounds and then with the magnesium compounds.

The halide may be applied in the form of a corresponding rhodium compound and/or a corresponding magnesium compound. Suitable examples thereof have been mentioned previously.

Alternatively, halogen-free rhodium or magnesium compounds may be used such as the acetates or nitrates and by a subsequent treatment with hydrogen halide or by impregnation with a metal halide the halide ions are applied onto the carrier. Another method is adjusting the halogen content of the catalyst required for the selective synthesis gas reaction upon impregnation of the rhodium and/or magnesium compound by using a halogen-containing organic compound such as 1,1-dichloroethane from which halogen can be released.

Suitable catalyst carriers are usual carrier materials having various specific surfaces; however, carriers which have a specific surface of from 50 to 1000 $m^2/g$ are preferred. Examples are silicic acid, natural or synthetic silicates of elements from groups II to VIII (i.e., the silicates of magnesium, calcium, aluminum, rare earths, titanium, zirconium, manganese) and aluminum oxide, zirconium oxide, thorium oxide, zeolites or spinels.

For preparing the catalyst, the carriers are soaked in a solution of the active components or impregnated therewith either simultaneously or in subsequent steps, as previously described. When using rhodium-III salts, an essential stage of the catalyst preparation consists in a subsequent reducing with suitable reduction agents such as hydrogen, carbon monoxide or methanol, performed in a separate apparatus or within the reactor. The reduction conditions are chosen such that rhodium is converted into a lower, nonmetallic valency stage. Generally a temperature below 300° C., preferably from 100° to 275° C., is applied. In many cases it is advantageous not to use the reducing gases in a concentrated state but with an additional amount of inert gas such as nitrogen, carbon dioxide or noble gases.

The concentration of rhodium, magnesium and halides in the catalysts may vary within wide limits; generally the values are from 0.1 to 20 weight % for rhodium, from 0.1 to 25 weight % for magnesium and from 0.01 to 20 weight % for the halide ions. Catalysts containing from 1.0 to 10 weight % of rhodium, from 0.1 to 20 weight % of magnesium and 0.05 to 15 weight % of halides are preferred.

For carrying out the process of the invention, gas mixtures consisting either completely or substantially of carbon monoxide and hydrogen, optionally containing other components in addition, such as nitrogen, argon, carbon dioxide or methane, are passed over the catalyst. The molar ratio of carbon monoxide and hydrogen may vary within wide limits. Preferred are molar ratios of from 5:1 to 1:5 and especially from 3:1 to 1:3.

The reaction temperatures are generally from 175 to 375° C., preferably from 200° to 350° C., and the reaction pressure is generally from 1 to 300 bars, preferably from 20 to 200 bars.

It is advantageous to adjust temperature and pressure in such a manner that a high selectivity with respect to the oxygen-containing compounds is insured and that the exothermic formation of methane promoted by elevated temperatures is maintained at a low level. High pressures and low temperatures are therefore preferred. The conversion rate of carbon monoxide should be generally below 50%, because a higher rate may cause increased formation of by-products which, in addition to methane, carbon dioxide and gaseous hydrocarbons, may comprise high molecular weight liquid hydrocarbons and oxygen-containing substances.

The process is preferably carried out in the gaseous phase, for which the usual solid bed reactors may be used. To insure a good heat dissipation the catalyst layer should be advantageously thin. Reactors provided with moving catalyst beds or fluidized bed reactors are likewise suitable.

Alternatively, the synthesis gas may be reacted in the presence of the solid and finely distributed catalyst suspended in inert solvents and/or reaction products.

According to an especially preferred embodiment of the invention, the reaction is carried out in the gaseous phase in a circulating gas apparatus, where the unreacted gas mixture is recycled to the reactor after separation of the condensible reaction products.

This operation mode is particularly economic and, because of the fresh gas being diluted by the recycled gas containing less hydrogen, it allows for the application of elevated temperatures and to obtain higher space/time yields at unchanged selectivity. Suitable circulating gas apparatus are those provided with interior or exterior gas circulation.

When carrying out the process of the invention it has been observed that, although the catalysts display a high initial activity and an excellent selectivity of the carbon monoxide reaction towards the oxygen-containing $C_2$ compounds, this activity and selectivity may gradually decrease on prolonged use of the catalysts at operation times of more than about 500 hours. Life of these catalysts may therefore be limited.

It has now been found that this life is considerably extended when during the reaction of the synthesis gas, magnesium salts or magnesium compounds vaporizable under the reaction conditions are fed either continuously or discontinuously to the reaction zone together with the gaseous reactants.

The advantage of this preferred embodiment of the invention resides in the fact that the activity and selectivity of the catalysts used for the reaction is nearly unchanged even after more than 1000 hours.

Examples of magnesium salts or magnesium compounds which are vaporizable under the reaction conditions and therefore capable of being fed in gaseous form to the reaction zone together with one or more of the reactants are magnesium chloride, bromide, iodide, acetylacetonate, ethylate, isopropylate, magnesium-aluminumethylate and -iso-propylate or magnesium salts of aliphatic monocarboxylic acids having from 1 to 4 carbon atoms in the molecule. Preferably, magnesium chloride or magnesium acetate is used, but alternatively those magnesium salts or magnesium compounds which can be converted to the halide by reaction with hydrogen halide, or to the corresponding carboxylates by reaction with aliphatic monocarboxylic acids, such as the oxide, hydroxide or the carbonates of magnesium are suitable.

The volatile magnesium salts or magnesium compounds are fed together with the gaseous reactants to the reaction zone, which operation can be carried out according to various methods. For example, the magnesium compound in dissolved form, for example as solution in water, ethanol or acetic acid, can be injected into the hot gas current before the catalyst layer. Alternatively, prior to their entry into the reaction zone, all or part of the reaction gases can be contacted at elevated temperature with a solution or melt of the magnesium compound, or these gases may be passed over such a solution or melt. According to an especially preferred operation mode, all or part of the reactants are passed at elevated temperature over the volatile magnesium compound present in solid form, which is thus vaporized without the use of an additional solvent. Alternatively, the volatile magnesium compounds may be applied onto an inert carrier material such as silicic acid, aluminum oxide or charcoal. The magnesium compound to be vaporized may be present either in the reactor or outside of it; preferably, it is arranged in such a manner that the heated reactants pass successively through the zone containing the magnesium compound and through that containing the catalyst. In principle, these zones may be merged into each other or optionally mixed.

The volatile magnesium compounds can be introduced either continuously or discontinuously into the reaction zone. In the case of the preferred continuous addition, the amount of magnesium compound is from 0.01 to 200 ppm, preferably 0.1 to 50 ppm, relative to the weight of the gas current passed over the catalyst. In the case of discontinuous addition, even larger amounts may be fed to the gas mixture, depending on the addition time. By means of the temperature and the volume of the gas passed over the magnesium compound the dosage of the latter can be controlled.

Subsequently, the gas current containing the volatile magnesium compound, carbon monoxide and hydrogen is reacted on contact with the catalyst containing rhodium, magnesium and halide.

When operating in a circulating gas apparatus according to the especially preferred embodiment of the invention, where after separation of the condensible reaction products the unreacted gas mixture is recycled to the reactor with addition of fresh synthesis gas, the magnesium compound can be added either to the circulating gas, to the fresh synthesis gas or to the mixture of both gases.

Life of the catalysts can be prolonged alternatively by another method than that of adding magnesium compounds, that is, during the reaction of the synthesis gas hydrogen halide or volatile organic halogen compounds not containing any sulfur or nitrogen in the molecule and splitting off hydrogen halide under the reaction conditions are fed continuously or discontinuously to the reaction zone together with the gaseous reactants.

This preferred operation mode of the process of the invention brings about the same advantage as that of adding magnesium compounds, that is, the activity and selectivity of the catalysts are nearly unchanged even after more than 1000 hours.

Hydrogen halides, hydrogen chloride, bromide or iodide or mixtures thereof may be used or produced in the reaction zone by reaction of halogens with hydrogen or synthesis gas. Hydrogen chloride is the preferred hydrogen halide.

Volatile organic halogen compounds not containing any sulfur or nitrogen in the molecule and splitting off hydrogen halide under the reaction conditions are alkyl, aryl and aralkyl halides having one or more halogen atoms in the molecule, such as dichloromethane, carbon tetrachloride, ethyl iodide, 1,1-dichloroethane, allyl chloride, tert.-butyl chloride or benzyl chloride, furthermore saturated or unsaturated halocarboxylic acids, haloaldehydes, haloalcohols, or haloethers of the aliphatic, cycloaliphatic or aromatic series, for example, mono-, di- or trichloroacetic acid, iodoacetic acid, bromoacetone, alpha, beta-dichloro-diethyl ether, 3-chloro-crotonic acid (cis or trans), or p-chlorobenzoic acid. Also suitable are carboxylic acid halides such as acetyl chloride, bromide or iodide or mono-, di- or trichloroacetyl chloride, which under the influence of the water formed in the synthesis gas reaction very easily split off hydrogen halide. The preferred halogen compound is acetyl chloride.

It is not required that the volatile organic halogen compounds split off hydrogen halide quantitatively; small amounts of hydrogen halide split off are sufficient to substantially extend the life of the catalysts.

The hydrogen halides or the organic compounds splitting off hydrogen halide are fed to the reaction zone together with the gaseous reactants according to various methods. Thus, the hydrogen halides or organic halogen compounds may be introduced into the hot gas current in dissolved form, for example as a solution in water, ethanol or acetic acid. Alternatively, the total reaction gas—or in a side current part of this gas stream—may be passed over the solid or liquid organic halogen compound before its entry into the reaction zone. By correspondingly adjusting the gas amount, the pressure and the temperature, the intended amount of halogen compound can be added in accordance with its partial pressure. Furthermore, the organic halogen compounds may be likewise applied in impregnated form onto an inert carrier such as silicic acid, aluminum oxide or charcoal, over which the reactants, that is, CO and $H_2$, are then passed.

The hydrogen halides or the volatile organic halogen compounds can be introduced either continuously or discontinuously into the reaction zone. In the case of the preferred continuous addition, their concentration is from 0.01 to 500 ppm, preferably 0.1 to 100 ppm, relative to the weight of the gas current passed over the catalyst. In the case of discontinuous addition, even larger amounts may be fed to the gas mixture, depending on the addition time. The amounts added are in this case inversely proportional to the time of addition.

Subsequently, the gas current containing the hydrogen halide or the volatile organic halogen compound, carbon monoxide and hydrogen is reacted on contact with the catalyst containing rhodium, magnesium and halide.

When operating in a circulating gas apparatus according to the especially preferred embodiment of the invention, where after separation of the condensible reaction products the unreacted gas mixture is recycled to the reactor upon addition of fresh synthesis gas, the hydrogen halide or the organic halogen compound can be added either to the circulating gas, the fresh synthesis gas, or to the mixture of both gases.

The two methods described for extending the life of the catalysts, i.e., the addition of magnesium compounds or the addition of hydrogen halide or organic halogen compound can be performed simultaneously.

The following examples illustrate the invention without limiting its scope. The conversion rates and selectivity are expressed in mol %. The other parts and percentages are by weight unless otherwise stated.

Examples 1 to 12 and Comparative Examples 1 and 2

(A) General test description

The apparatus consists of a heatable reactor tube of corrosion-proof steel having a length of 1 m and an inner diameter of 16 mm, provided with a coaxially arranged thermometer casing having an exterior diameter of 6 mm, a connected condenser, a receiver for the condensate, and a compressor for recycling part of the uncondensed gases to the reactor (circulating gas). 100 ml each of the catalysts indicated below are charged. After flushing of the apparatus with nitrogen, first a pressure of 100 bars is adjusted by means of synthesis gas having the following composition: 49% by vol. of CO, 49% by vol. of $H_2$, 1% by vol. of $CO_2$, 1% by vol. of $N_2$ (and small amounts of other components), and the reactor is heated to 275° C. During the heating and in the course of the test, 450 Nl/h of synthesis gas having the above composition are fed to the circulating gas via the suction face of the compressor, and passed over the catalyst together with the circulating gas. The gas mixture leaving the reactor is cooled (by brine cooling) in the condenser to about +5° C., and the condensed portions are collected in the receiver. The uncondensed residual gas is recycled to the reactor via the compressor after having been mixed with fresh synthesis gas. In order to maintain the pressure and to discharge by-products, part of the residual gas is let off as waste gas via a pressure regulating valve.

According to this operational method the catalysts as described below are tested. In the Table, there are listed the duration of the tests, the space/time yields of oxygen-containing $C_2$ products per liter of catalyst and hour at the start and the end of the tests, the percental distribution of acetic acid, acetaldehyde and ethanol, relative to the $C_2$ portion of the condensate, and the selectivity with respect to these compounds (in mol % of CO, relative to reacted CO). Small amounts of ethyl acetate or acetaldehyde-diethylacetal obtained are calculated as acetic acid, ethanol or acetaldehyde.

(B) Preparation of catalysts

EXAMPLE 1

40 g of a silicic acid having a BET surface of 270 $m^2/g$, a pore volume of 1.22 ml/g, a bulk density of 0.4 kg/l, a pH of 7.4 (measured on granules having a diameter of 2 to 3 mm) and containing 99.35 % of $SiO_2$ and 0.2% of Na are impregnated with a solution of 7.5 g of magnesium chloride (56% strength) in 45 ml of water, dried for 2 hours at 70° C. and 2 hours at 150° C. Subsequently the catalyst is sintered for 30 minutes at 900° C. After cooling, it is impregnated with a solution of 5.7 g of $RhCl_3 \cdot XH_2O$ (37.8% of Rh) in 45 ml of water, and dried in the same manner as described above. In a flow tube made of glass, the catalyst is reduced by passing over it 30 Nl/h of hydrogen for 3 hours at 225° to 275° C. under normal pressure. After the reduction, it contains 4.6% of Rh, 2.3% of Mg and 4.9% of Cl.

At the start of the test, the space/time yield is 470 g of oxygen-containing $C_2$ compounds per liter of catalyst and hour, which compounds are distributed as follows: 60% of acetic acid, 32.8% of acetaldehyde and 7.2% of ethanol. After a test duration of 620 hours the Cl content is still 3.8%.

COMPARATIVE EXAMPLE 1

(Using a magnesium-free and halogen-free catalyst)

6.1 g of $Rh(NO_3)_3 \cdot 2 H_2O$ (31.8% of Rh) are dissolved in 45 ml of water and applied onto 40 g of the silicic acid carrier as described in Example 1. After a 2 hours' standing, the catalyst is dried at 80° C. and 260 mbars by passing 1 Nl/h of nitrogen over it. Upon reduction as indicated in Example 1, the catalyst contains 4.6% of Rh.

COMPARATIVE EXAMPLE 2

(Using a halogen-free catalyst)

A solution of 10.6 g of $Mg(NO_3)_2 \cdot 6 H_2O$ in 43 ml of water is applied onto 40 g of the silicic acid carrier as described in Example 1. The impregnated carrier is dried at 120° C. and subsequently sintered for 30 minutes at 800° C. After cooling, it is impregnated with a solution of 6.3 g of $Rh(NO_3)_3 \cdot 2 H_2O$ (31.8% of Rh) in 45 ml of water, dried at 80° C. under a reduced pressure of 260 mbars and 1 Nl/h of nitrogen, and reduced as described in Example 1. After the reduction, the catalyst contains 4.6% of Rh and 2.3% of Mg.

EXAMPLE 2

As carrier there is used a natural commercial magnesium silicate having the following composition: 56 to 60% of $SiO_2$, 1.2 to 3.5% of $Al_2O_3$, 0.5 to 1.3% of $Fe_2O_3$, 22.0 to 26.3% of MgO, 5.5 to 8.0% of $CO_2$, alkali metal oxides, CaO and $TiO_2$ altogether. The loss at red heat is 19%, the specific weight 2.45 to 2.6 g/ml and the granular size 2 to 3 mm.

54 g (about 0.1 l) of the above-described carrier are impregnated with a solution of 7.0 g of $RhCl_3 \cdot XH_2O$ (37.8% of Rh) in 45 ml of water and dried at 150° C. The catalyst is thereafter reduced as described in Example 1, however, by passing over it 60 Nl/h of a mixture of nitrogen and hydrogen in a volume ratio of 1:1, instead of 30 Nl/h of hydrogen. Upon the reduction the catalyst contains 4.6% of Rh, 13.5% of Mg and 2.3% of Cl. After a test duration of 450 hours the Cl content is still 2.1%.

EXAMPLE 3

(Reduction in the reactor)

54 g (about 0.1 l) of the catalyst described in Example 2 are impregnated with a solution of 7.0 g of $RhCL_3 \cdot XH_2O$ (37.8% of Rh) in 45 ml of water, and dried at 150° C. A 100 ml portion of this catalyst is introduced into the reactor without reduction, heated without pressure to 225° C., under a nitrogen current of 30 Nl/h, and reduced at this temperature by passing over it 60 Nl/h of a mixture of carbon monoxide and hydrogen in a volume ratio of 1:1. Different from the general test description, a pressure of 100 bars is then established by means of synthesis gas at 225° C., and the catalyst is heated to the reaction temperature of 275° C. After the reduction, the catalyst contains 4.6% of Rh, 13.5% of Mg and 2.25% of Cl. After a test duration of 420 hours the Cl content is still 2.0%.

EXAMPLE 4

The natural magnesium silicate carrier as described in Example 2 is washed and dried, whereafter it has the following composition: 65.5% of $SiO_2$, 3.6% of $Al_2O_3$, 0.5% of $Fe_2O_3$ and 14.0% of MgO. The bulk density is 537 g/l and the pore volume 0.99 ml/g. 54 g of this carrier are impregnated with a solution of 7.0 g of $RhCl_3 \cdot XH_2O$(37.8% of Rh) in 49 ml of water and dried at 150° C. The catalyst is reduced as described in Example 1, whereupon it contains 4.6% of Rh, 7.8% of Mg and 2.9% of Cl.

EXAMPLE 5

54% of the magnesium silicate carrier prepared according to Example 4 are impregnated with a solution of 14.4 g of $RhBr_3 \cdot XH_2O$ (27.2% of Rh) in 49 ml of water and dried. The reduction is analogous to that in Example 1. The reduced catalyst contains 6.0% of Rh, 7.3% of Mg and 7.3% of Br. The Br content decreases only to 6.6% in the course of the 310 hours' test.

EXAMPLE 6

10 g of $RhCl_3 \cdot XH_2O$(37.8% of Rh) are dissolved in 20 ml of water, mixed in the cold state with a solution of 18.2 g of potassium iodide in 20 ml of water and immediately thereafter applied onto 54 g of the magnesium silicate carrier having the composition as described in Example 4.

The impregnated catalyst is kept at room temperature for 48 hours and thereafter dried at 80° C. in vacuo under nitrogen. Upon drying it contains 4.6% of Rh, 5.5% of Mg, 5.2% of K, 16.9% of I and 4.7% of Cl. The reduction is carried out as described in Example 1, by passing over the catalyst 30 Nl/h of hydrogen under atmospheric pressure at 225° to 275° C. for 3 hours. After the reduction the catalyst contains 4.7% of Cl and 5.6% of I.

EXAMPLE 7

40 g of the carrier described in Example 1 are impregnated with a solution of 4.4 g of $[Rh (CO)_2Cl]_2$(Rh content 52.94%) and 6.8 g of anhydrous magnesium acetate in 43 ml of methanol and dried at 80° C. The catalyst contains 4.6% of Rh, 2.3% of Mg and 1.9% of Cl. It is fed to the reactor without having been pretreated in reductive manner.

EXAMPLE 8

40 g of the carrier described in Example 1 are impregnated with a solution of 9.1 g of $Mg_3[RhCl_6]_2 \cdot 7H_2O$ (24.8% of Rh, 8.8% of Mg) in 45 ml of methanol, dried at 80° C. and reduced as described in Example 1. Upon the reduction the catalyst contains 4.6% of Rh, 1.6% of Mg and 4.0% of Cl.

EXAMPLE 9

(Preparation of the catalyst by lyophilization)

4.9 g of $Mg [Rh^I (CO)_2Cl_2]_2$ /42.5% of Rh) are dissolved in 46 ml of methanol under nitrogen at 0° C. and applied thereafter onto 40 g of a cooled silicic acid carrier having the composition described in Example 1, cooled to −10° C. and dried under a pressure of 13 mbars until its weight remains constant. The prepared catalyst contains 4.6% of Rh, 0.55% of Mg and 3.2% of Cl. A 100 ml portion of this catalyst is fed to the reactor without a further reductive treatment.

EXAMPLE 10

Operations are as in Example 1, however, after cooling the $MgCl_2$-containing sintered carrier is impregnated with a solution of 2.4 g of $RhCl_3 \cdot XH_2O$ (37.8% of Rh) in 45 ml of water. Upon drying the catalyst is reduced as described in Example 1. It contains 2.0% of Rh, 2.3% of Mg and 3.8% of Cl.

EXAMPLE 11

Operations are as in Example 1, however, impregnation with $RhCl_3$ is carried out by using a solution of 10.2% of $RhCl_3 \cdot XH_2O$ (37.8% of Rh) in 45 ml of water. The further processing is as in Example 1. Upon the reduction the catalyst contains 8.0% of Rh, 2.25% of Mg and 5.4% of Cl.

EXAMPLE 12

40 g of the silicic acid carrier described in Example 1 are impregnated with a solution of 7.5 g of $MgCl_2$ (56% strength) and 5.0 g of $RhCl_3 \cdot XH_2$ (37.8% of Rh) in 45 ml of water and dried for 2 hours at 70° C. and for 2 hours at 150° C. The catalyst reduced as described in Example 1 contains 4.0% of Rh, 2.3% of Mg and 4.3% of Cl.

(C) Test results:

The results are listed in the following table.

carbon monoxide, 49 vol. % of hydrogen, 1 vol. % of carbon dioxide and small amounts of nitrogen are passed over the catalyst at 120 bars and 280° C. Into a preheater mounted before the reactor and heated to 280° C., too, 10 ml/h of an aqueous 0.07% magnesium acetate solution are injected into the hot gas mixture. After having left the reactor, the reaction gases are cooled to about +5° C. and the uncondensed portions are depressurized. 27 g of acetic acid, 13 g of acetaldehyde and 4 g of ethanol are obtained per hour as condensate in the form of an aqueous solution, which corresponds to a space/time yield of 440 g of oxygen-containing $C_2$ products per liter of catalyst and hour. Small amounts (about 2% relative to the cited $C_2$ products) of ethyl acetate or acetaldehyde diethylacetal formed were calculated as acetic acid, ethanol or acetaldehyde and are contained in the indicated values. The same applies for the following examples.

The CO conversion rate is 39.5%, the selectivity with respect to the oxygen-containing $C_2$ products 82%, relative to reacted carbon monoxide. Space/time yield, Co conversion rate and the selectivity are unchanged

TABLE

Reaction conditions: 100 bars, 275° C., feed gas 450 Nl/h $CO:H_2$ = 1:1, catalyst volume 0.1 l
AcOH = acetic acid, AcH = acetaldehyde, EtOH = ethanol

| Example | Catalyst composition | | | Test duration in hours | Space/time yield of oxygen-containing $C_2$-compd. in g/l.h | | Composition of the $C_2$-compounds in wt.-% | | | Selectivity in mol % CO reacted to give | |
|---|---|---|---|---|---|---|---|---|---|---|---|
| | Rh [wt.-%] | Mg [wt.-%] | carrier | | test start | test end | AcOH | AcH | EtOH | $C_2$-compd. | $CH_4$ |
| 1 | 4.6 | 2.3 | $SiO_2$ | 620 | 470 | 445 | 60.0 | 32.8 | 7.2 | 85.0 | 7.1 |
| Comp. Ex. 1 | 4.6 | — | $SiO_2$ | 180 | 52 | 33 | 42.3 | 11.5 | 46.1 | 48.0 | 30.0 |
| Comp. Ex. 2 | 4.6 | 2.3 | $SiO_2$ | 265 | 275 | 183 | 62.9 | 20.3 | 16.7 | 61.0 | 33.0 |
| 2 | 4.6 | 13.8 | $MgSiO_3$ | 450 | 415 | 338 | 19.2 | 12.7 | 63.1 | 78.0 | 17.5 |
| 3 | 4.6 | 13.5 | $MgSiO_3$ | 420 | 436 | 418 | 25.6 | 17.0 | 57.3 | 82.0 | 9.9 |
| 4 | 4.6 | 7.8 | $MgSiO_3$ | 580 | 495 | 462 | 29.6 | 12.5 | 57.8 | 90.5 | 5.9 |
| 5 | 6.0 | 7.3 | $MgSiO_3$ | 310 | 522 | 486 | 39.8 | 20.7 | 39.4 | 77.2 | 12.7 |
| 6 | 4.6 | 7.7 | $MgSiO_3$ | 215 | 422 | 387 | 53.1 | 17.1 | 29.8 | 82.5 | 10.9 |
| 7 | 4.6 | 2.3 | $SiO_2$ | 380 | 465 | 452 | 66.7 | 25.2 | 8.1 | 83.0 | 10.5 |
| 8 | 4.6 | 1.6 | $SiO_2$ | 250 | 480 | 435 | 56.7 | 26.7 | 16.6 | 86.0 | 9.8 |
| 9 | 4.6 | 0.55 | $SiO_2$ | 220 | 495 | 475 | 53.3 | 27.2 | 19.3 | 84.5 | 9.4 |
| 10 | 2.0 | 2.3 | $SiO_2$ | 350 | 370 | 352 | 62.1 | 28.7 | 9.2 | 78.5 | 13.0 |
| 11 | 8.0 | 2.3 | $SiO_2$ | 350 | 532 | 490 | 53.7 | 30.5 | 15.8 | 86.0 | 8.2 |
| 12 | 4.0 | 2.3 | $SiO_2$ | 280 | 410 | 375 | 50.7 | 35.1 | 14.2 | 78.2 | 12.8 |

EXAMPLE 13

100 g of a silicic acid having a BET surface of 270 m²/g, a pore volume of 1.27 ml/g, a bulk density of 0.4 kg/l, a pH of 7.4 (measured on granules having a diameter of 2 to 3 mm) and containing 99.35% of $SiO_2$ and 0.2% of Na are impregnated with a solution of 18.75 g of magnesium chloride (56% strength) in 112 ml of water, dried for 2 hours at 70° C. and for 2 hours at 150° C. Subsequently the catalyst is sintered for 30 minutes at 900° C. After cooling, it is impregnated with a solution of 14.25 g of $RhCl_3 \cdot XH_2O$ (37.8% of Rh) in 112 ml of water, and dried in the same manner as described above. In a flow tube made of glass, the catalyst is reduced by passing over it 75 Nl/h of hydrogen for 3 hours at 225° to 275° C. under normal pressure. After the reduction, it contains 4.6% of Rh, 2.3% of Mg and 4.9% of Cl.

100 ml of the catalyst are introduced into a vertically positioned flow tube reactor made of corrosion-proof steel, having an inner diameter of 16 mm and a length of 1 m, provided with exterior salt melt heating, thermometer, subsequent condenser, receiver for the condensate and pressure relief valve. After flushing with nitrogen, 235 Nl/h of a gas mixture containing 49% by vol. of even after 1400 hours.

COMPARATIVE EXAMPLE 3

Operations are as in Example 13; however, instead of the aqueous magnesium acetate solution 10 ml of distilled water per hour are introduced into the preheater. After 200 hours the space/time yield is likewise 440 g of oxygen-containing $C_2$ products, after 550 hours it is 425 g and after 1000 hours it is only 320 g, each per liter of catalyst and hour. The percental composition of the $C_2$ products is the same as in Example 13. The CO conversion rate decreases within this period of time from 39.5% to 34.6% and the selectivity towards the oxygen-containing $C_2$ products drops from 82% to 68%.

EXAMPLE 14

100 ml of the catalyst described in Example 13 are fed to the reactor of the apparatus described in Example 13. The test arrangement is the same as in Example 13, however, instead of the magnesium acetate solution, 100 ml of silicic acid that have been impregnated with a solution of 20 g of magnesium chloride (56% strength)

in 35 g of water and subsequently dried, are fed to the preheater. The reactants carbon monoxide and hydrogen having the same composition as in Example 13 are thereafter passed over the preheater into the reactor. Under the reaction conditions of Example 13 there are obtained per hour 30.5 g of acetic acid, 10.5 g of acetaldehyde and 3.8 g of ethanol as aqueous condensate. The CO conversion rate is 38.7% and the selectivity with respect to the oxygen containing $C_2$ products 83.4% relative to converted carbon monoxide. The space/time yield, the CO conversion rate and the selectivity are unchanged even after more than 1200 hours.

EXAMPLE 15

As carrier there is used a natural commercially available magnesium silicate, which upon washing and drying, has the following composition:

65.5% of $SiO_2$, 3.6% of $Al_2O_3$, 0.5% of $Fe_2O_3$ and 14.0% of MgO. The bulk density is 537 g/l and the pore volume 0.99 ml/g.

A 108 g portion of this carrier (200 ml) is impregnated with a solution of 12.6 g of $RhCl_3 \cdot XH_2O$ (37.8% of Rh) in 98 ml of water and dried at 150° C. The catalyst is reduced in a flow tube made of glass by passing over it 75 Nl/h of nitrogen for 3 hours at 225° to 275° C. under normal pressure. The reduced catalyst contains 4.2% of Rh, 7.9% of Mg and 3.8% of Cl.

A 100 ml portion of this catalyst is introduced into the reactor described in Example 14, which, however, is provided additionally with a compressor for the circulation of part of the residual gas mixture. Thereafter 100 ml of a silicic acid carrier are fed to the preheater, this carrier having previously been impregnated with a solution of 15 g of magnesium acetate in 40 g of water and subsequently dried.

After flushing of the apparatus with nitrogen, first a pressure of 120 bars is adjusted by means of synthesis gas having the following composition: 49% by vol. of CO, 49% by vol. of $H_2$, 1% by vol. of $CO_2$ and traces of $N_2$, and the reactor is heated to 280° C. During the heating and in the course of the test, 300 Nl/h of synthesis gas having the above composition are fed to the circulating gas via the suction face of the compressor, and passed successively through the preheater heated to 280° C. and through the reactor. The gas mixture leaving the reactor is cooled by brine cooling in the condenser to about +5° C., and the condensed portions are collected in the receiver. The uncondensed residual gas is recycled to the reactor via the compressor after having been mixed with fresh sythesis gas. In order to maintain the pressure and to discharge byproducts, part of the residual gas is let off as waste gas via a pressure regulating valve.

Per hour there are obtained 49 g of oxygen-containing $C_2$ compounds (15 g of acetic acid, 6 g of acetaldehyde and 28 g of ethanol) in the form of an aqueous solution, which corresponds to a space/time yield of 490 g/l. The CO conversion rate is on the average 35% of the feed quantity and the selectivity with respect to the oxygen-containing $C_2$ compounds is 86.6%, relative to reacted carbon monoxide. Space/time yield, CO conversion rate and the selectivity are unchanged even after 1200 hours.

COMPARATIVE EXAMPLE 4

Operations are as in Example 15, however, the preheater is charged with pure unimpregnated silicic acid. Under test conditions being as in Example 15 for the rest and with the use of 100 ml of catalyst having the composition as indicated there, the space/time yield of the first 380 hours is 475 of oxygen-containing $C_2$ products per liter of catalyst and hour, after a total of 720 hours it is 435 g/lh and after 1200 hours it is 360 g/lh, the composition in percent of the product mixture being the same as in Example 15. The conversion rate of CO decreases within the same period of time from 35 to 28.6% and the selectivity with respect to the oxygen-containing products from 86% to 77.9%, relative to reacted carbon monoxide.

EXAMPLE 16

100 g of a silicic acid as described in Example 13 are impregnated with a solution of 14.7 g of magnesium chloride (56% strength) in 112 ml of water and dried for 2 hours at 70° C. and 2 hours at 150° C. Subsequently, it is sintered for 30 minutes at 800° C. After cooling, the silicic acid is impregnated with a solution of 14.0 g of $RhCl_3 \cdot XH_2O$ (38.0% of Rh) in 112 ml of water, and dried in the same manner as indicated above. The catalyst is reduced in a flow tube of glass by passing over it for 3 hours 75 Nl/h of hydrogen at 225° to 275° C. and under normal pressure. After the reduction, it contains 4.5% of Rh; 1.8% of Mg and 4.7% of Cl.

100 ml of the reduced catalyst are introduced into a reactor according to Example 13. After flushing with nitrogen, 320 Nl/h of a gas mixture containing 49 vol. % of carbon monoxide, 49 vol. % of hydrogen, 1 vol. % of carbon dioxide and small amounts of nitrogen are passed over the catalyst at 100 bars and 290° C. Into a preheater mounted before the reactor, which is likewise heated to 290° C., too, 10 ml/h of an aqueous 0.1% hydrochloric acid are injected into the hot gas current.

After leaving the reactor, the reaction gases are cooled to about +5° C., and the uncondensed portions are depressurized. 34 g of acetic acid, 8 g of acetaldehyde and 4.5 g of ethanol are obtained per hour as condensate in the form of an aqueous solution, which corresponds to a space/time yield of 465 g of oxygen-containing $C_2$ products per liter of catalyst and hour. Small amounts (about 2%, relative to the cited $C_2$ products) of ethyl acetate or acetaldehyde diethylacetal formed were calculated as being acetic acid, ethanol or acetaldehyde and are contained in the indicated values. The same applies to the following examples.

The CO conversion rate is 30% and the selectivity, with respect to the oxygen-containing $C_2$ products, 80.6%, relative to reacted carbon monoxide. After 1450 hours the space/time yield per liter of catalyst and hour is 450 g. The selectivity is unchanged.

COMPARATIVE EXAMPLE 5

Operations are as in Example 16, however, instead of the dilute hydrochloric acid, 10 ml of distilled water per hour are fed to the preheater. After 200 hours the space/time yield is likewise 465 g of oxygen-containing $C_2$ products, after 750 hours still 410 g and after 1200 hours only 370 g, each time per liter of catalyst and per hour. The precental composition of the $C_2$ products is the same as in Example 16. The CO conversion rate decreases within this period of time from 30% to 27.5% and the selectivity with respect to the oxygen-containing $C_2$ products drops from 80.6 to 69.6%.

EXAMPLE 17

A catalyst is prepared using the carrier as indicated in Example 15, which is impregnated and dried as described in Example 15. Upon the reduction in the manner described in Example 15, the catalyst contains 4.1% of Rh, 7.5% of Mg and 3.6% of Cl.

100 ml of the catalyst are introduced into the reactor according to Example 16 which, however, is provided with a compressor in addition for the circulation of part of the residual gas mixture.

After flushing with nitrogen, first a pressure of 100 bars is adjusted by means of a synthesis gas (49 vol. % of CO, 49 vol. % of $H_2$, 1 vol. % of $CO_2$, traces of $N_2$), and the catalyst is heated to 290° C. During the heating and in the course of the test, 350 Nl/h of synthesis gas having the above composition are fed to the circulating gas via the suction face of the compressor, and passed successively through the preheater heated to 290° C. and through the reactor together with the circulating gas. 18 ml/h of a 0.3% solution of methylene chloride in methanol are fed to the preheater. The gas mixture leaving the reactor is cooled by brine cooling in the condenser to about +5° C., and the condensed portions are collected in the receiver. The uncondensed residual gas is recycled to the reactor via the compressor after having been mixed with fresh synthesis gas. In order to maintain the pressure and to discharge byproducts, part of the residual gas is let off as waste gas via a pressure regulating valve.

Per hour there are obtained 48 g of oxygen-containing $C_2$ compounds (14 g of acetic acid, 5 g of acetaldehyde and 29 g of ethanol) in the form of an aqueous solution, which corresponds to a space/time yield of 480 g/l.h. The CO conversion rate is on the average 32% of the feed quantity and the selectivity with respect to the oxygen-containing $C_2$ products 79.6%, relative to converted carbon monoxide. Space/time yield, CO conversion rate and the selectivity are still unchanged after 1750 hours.

COMPARATIVE EXAMPLE 6

Operations are as in Example 17, however, 18 ml/h are fed to the preheater. Under identical test conditions for the remainder as in Example 17 and by using 100 ml of the catalyst having the composition of Example 17 there is obtained a space/time yield of 470 g after the first 400 hours, of 460 g after a total of 800 hours and of 425 g after 1250 hours, of oxygen-containing $C_2$ products, per liter of catalyst and hour, the composition of the product mixture being as in Example 17. Within the cited period of time the CO conversion rate decreases from 31 to 29.5% and the selectivity with respect to the oxygen-containing $C_2$ products drops from 80.5% to 76.5%, relative to reacted carbon monoxide.

EXAMPLE 18

Operations are as in Example 17, however, instead of the methanolic methylene chloride solution, 25 ml/h of diethyl ether are fed to the preheater. Under these conditions the space/time yield drops from 490 g/l.h after 100 hours to 450 g/l.h after 800 hours. In the further course of the test 25 ml of a 0.2% solution of acetyl chloride in diethyl ether are fed to the preheater. The space/time yield remains practically constant and amounts to 440 to 445 g per liter of catalyst and hour after a total test duration of 1800 hours.

What is claimed is:

1. A process for the manufacture of acetic acid, ethanol, acetaldehyde and any secondary products thereof which comprises catalytically reacting carbon monoxide and hydrogen using a catalyst, applied onto a carrier, containing salts or complex compounds of rhodium either with a valence of less than 3 or prepared by reduction of correspondingly supported compounds of trivalent rhodium at a temperature below 300° C., halide ions and a co-catalyst of magnesium in the form of a salt or complex compound.

2. The process according to claim 1 wherein the catalyst contains 0.1 to 20 weight percent rhodium, 0.1 to 25 weight percent magnesium and 0.01 to 20 weight percent halide ions.

3. The process according to claim 1 wherein the carrier is either silicic acid or magnesium silicate.

4. The process according to claim 1, 2 or 3 wherein the catalyst is in the form of a complex compound of either $Mg_3[RhCl_6]_2$ or $Mg[Rh(CO)_2Cl_2]_2$.

5. The process according to claim 1 or 3 wherein the halide ions are chlorides.

6. The process according to claim 5 wherein the catalyst is in the form of a complex compound of either $Mg_3[RhCl_6]_2$ or $Mg[Rh(CO)_2Cl_2]_2$.

7. The process according to claim 1 or 3 further comprising the continuous or discontinuous addition of volatile magnesium salts or magnesium compounds together with the carbon monoxide and hydrogen as gaseous starting materials to the reaction zone during the reaction.

8. The process according to claim 4 further comprising the continuous or discontinuous addition of volatile magnesium salts or magnesium compounds together with the carbon monoxide and hydrogen as gaseous starting materials to the reaction zone during the reaction.

9. The process according to claim 7 wherein the magnesium salt or magnesium compound used is either magnesium acetate or magnesium chloride.

10. The process according to claim 1, 2 or 3 further comprising the continuous or discontinuous addition to the reaction zone of a hydrogen halide or a volatile organic halogen compound not containing any sulfur or nitrogen in the molecule and splitting off hydrogen halide under reaction conditions together with the gaseous starting materials during the reaction.

11. The process according to claim 7 further comprising the continuous or discontinuous addition to the reaction zone of a hydrogen halide or a volatile organic halogen compound not containing any sulfur or nitrogen in the molecule and splitting off hydrogen halide under reaction conditions together with the gaseous starting materials during the reaction.

12. The process according to claim 10 wherein the hydrogen halide is hydrogen chloride.

13. The process according to claim 10 wherein the organic halogen compound is acetyl chloride.

* * * * *